US00PP18054P2

(12) United States Plant Patent
Trees et al.

(10) Patent No.: US PP18,054 P2
(45) Date of Patent: Sep. 18, 2007

(54) ***SALVIA* PLANT NAMED 'BALSALMISP'**

(50) Latin Name: *Salvia×hybrida*
Varietal Denomination: Balsalmisp

(75) Inventors: Scott C. Trees, Shell Beach, CA (US); Tau-San Chou, Batavia, IL (US)

(73) Assignee: Ball Horticultural Company, West Chicago, IL (US)

( * ) Notice: Subject to any disclaimer, the term of this patent is extended or adjusted under 35 U.S.C. 154(b) by 19 days.

(21) Appl. No.: 11/286,836

(22) Filed: Nov. 22, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

Christman Steve Salvia 'Indigo Spires' 2004 http://www-.floridata.com/ref/s/salv_indigo.cfm.*

Fehr W. R. Principles of Cultivar Development. p. 287–303 1987.*

European Plant Breeders' Rights application No. 2005/2340 filed Nov. 16, 2005.

* cited by examiner

*Primary Examiner*—Anne Marie Grunberg
*Assistant Examiner*—Annette H Para
(74) *Attorney, Agent, or Firm*—Audrey Charles

(57) ABSTRACT

A new and distinct cultivar of *Salvia* plant named 'Balsalmisp' characterized by its indigo-colored flowers, floriferousness, dark green-colored foliage, and vigorous, compact and upright growth habit.

2 Drawing Sheets

Latin name of genus and species of plant claimed: *Salvia× hybrida.*

Variety denomination. 'Balsalmisp'.

BACKGROUND OF THE INVENTION

The present invention relates to a new and distinct cultivar of *Salvia* plant botanically known as *Salvia×hybrida* and hereinafter referred to by the cultivar name 'Balsalmisp'.

The new cultivar originated in a controlled breeding program in Illinois during May 2003. The objective of the breeding program was the development of *Salvia* cultivars with compact and well branched growth habits.

The new cultivar is an irradiation induced sport of 'Indigo Spires', not patented, characterized by its indigo-colored flowers, dark green-colored foliage, and upright growth habit. The irradiation occurred on May 20, 2003. The new cultivar was discovered and selected during August 2003 in a controlled environment at Arroyo Grande, Calif.

Asexual reproduction of the new cultivar by terminal stem cuttings since August 2003 at Arroyo Grande, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balsalmisp' as a new and distinct cultivar of *Salvia* plant:

1. Indigo-colored flowers;
2. Floriferousness;
3. Dark green-colored foliage; and
4. Vigorous, compact and upright growth habit.

While other differences exist, plants of the new cultivar differ from plants of the parent 'Indigo Spires' primarily in growth habit. The new cultivar has shorter internodes, making it a more compact plant.

Of the many commercially available *Salvia* cultivars known to the inventors, the most similar in comparison to the new cultivar is the parent cultivar 'Indigo Spires', not patented. However, in side by side comparisons, plants of the new cultivar differed from plants of 'Indigo Spires' in the following characteristics:

1. Plants of the new cultivar are more compact than plants of 'Indigo Spires';
2. Plants of the new cultivar have shorter internodes than plants of 'Indigo Spires'; and
3. Plants of the new cultivar have smaller leaves than plants of 'Indigo Spires'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balsalmisp'. The plants were grown in 10 cm pots for 7 weeks in a greenhouse at West Chicago, Ill.

DETAILED BOTANICAL DESCRIPTION

Figure 1:
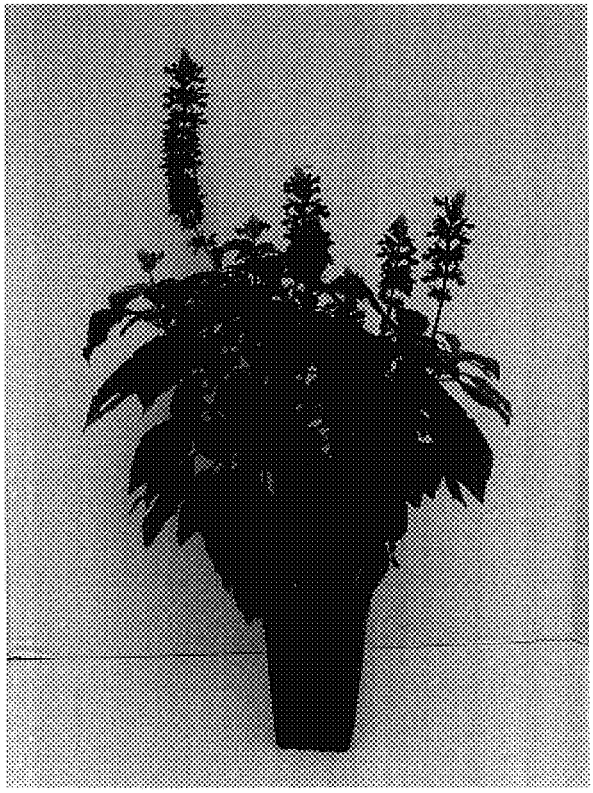
FIG. 1 illustrates a side view of the overall growth and flowering habit of 'Balsalmisp'.
Figure 2:
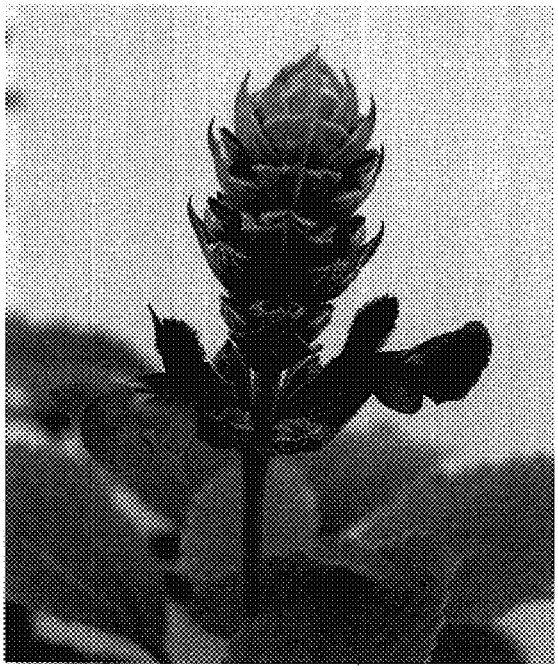
FIG. 2 illustrates a close-up view of a single inflorescence of 'Balsalmisp' beginning to flower.
Figure 3:
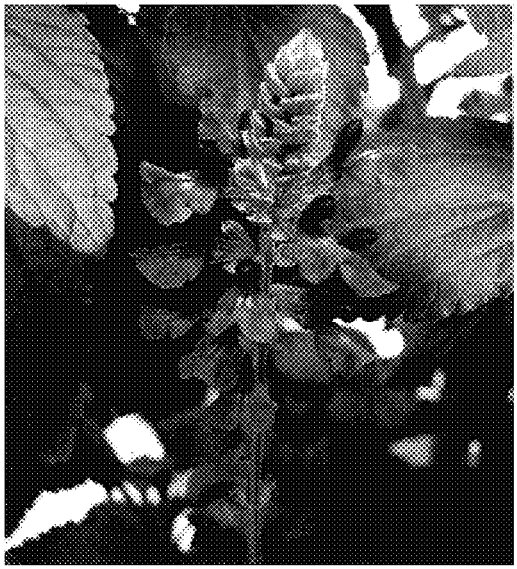
FIG. 3 illustrates a single inflorescence of 'Balsalmisp' with approximately one-third of the flowers open.
Figure 4:
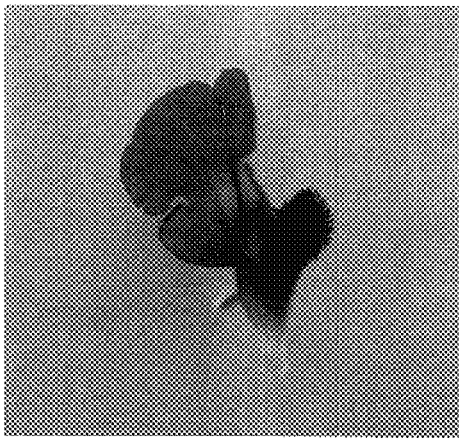
FIG. 4 illustrates a side view of a single flower of 'Balsalmisp'.
Figure 5:
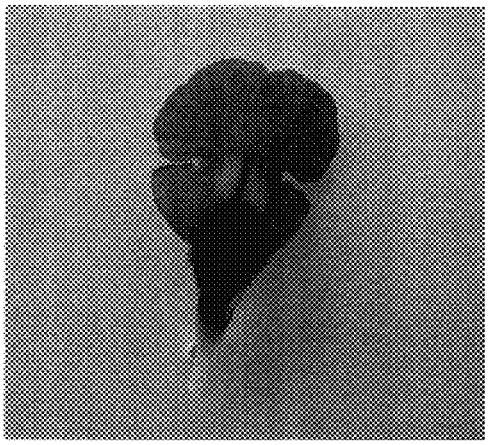
FIG. 5 illustrates a front view of a single flower of 'Balsalmisp'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 11, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 7 weeks utilizing a soilless growth medium. Greenhouse temperatures were maintained at approximately 70° F. to 80° F. (21° C. to 26° C.) during the day and approximately 62° F. to 68° F. (17° C. to 20° C.) during the night. Greenhouse light levels of 5,000 to 10,000 footcandles were maintained during the day.

Botanical classification: *Salvia×hybrida* cultivar Balsalmisp.

Parentage:

*Parent.*—'Indigo Spires', not patented.

Propagation:

*Type cutting.*—Terminal stem.

*Time to initiate roots.*—Approximately 5 to 8 days.

*Time to produce a rooted cutting.*—Approximately 21 to 42 days.

*Root description.*—Fine and fibrous.

*Rooting habit.*—Branching.

Plant description:

*Crop time.*—Approximately 6 to 8 weeks from a rooted cutting.

*Type.*—Perennial.

*Growth habit and general appearance.*—Vigorous, upright, and compact.

*Size.*—Height from soil level to top of plant plane: Approximately 50.8 cm. Height from soil level to top of foliage: Approximately 32.6 cm. Width: Approximately 38.2 cm.

*Branch.*—Quantity: Approximately 2 primary branches with lateral branches forming potentially at every node. Shape: Square in cross section. Strength: Strong. Length of primary branch: Approximately 15.3 cm. Diameter of primary branch: Approximately 6.6 mm. Texture: Densely pubescent with appressed soft, short hairs with longer hairs at nodes. Color: 138A with streaks of N187A. Internode length at center of branch: Approximately 3.5 cm.

*Foliage.*—Number of leaves per main branch: Approximately 8. Fragrance: Strong, sage-like. Form: Simple. Arrangement: Opposite. Aspect: At obtuse angle to stem. Shape: Ovate/elliptic. Margin: Crenate. Apex: Acute. Base: Obtuse. Venation pattern: Pinnate. Length of mature leaf: Approximately 8.5 cm. Width of mature leaf: Approximately 4.8 cm. Texture of upper surface: Puberulent, rugose. Texture of lower surface: Puberulent with long hairs along the veins. Color of upper surface of mature foliage: Closest to 139A with venation of 145C. Color of lower surface of mature foliage: Closest to between 137A and 137B with venation of 145C. Petiole length: Approximately 3.6 cm. Petiole diameter: Approximately 1.9 mm. Petiole shape: Square in cross section. Petiole texture: Densely pubescent with appressed soft, short hairs. Petiole color: 145C.

Flowering description:

*Flowering habit.*—'Balsalmisp' is freely flowering under outdoor growing conditions with substantially continuous blooming from spring through autumn and year round in greenhouse environment.

*Time to first flower.*—Approximately 12.5 weeks from sticking of unrooted cutting.

*Lastingness of individual bloom.*—Approximately 5 days.

Inflorescence description:

*Type.*—Flowers arranged in verticillasters on spikes.

*Number per plant with at least one open flower.*—Approximately 5 spikes at 7 weeks.

*Number of fully open flowers per verticillaster.*—Approximately 3.

*Peduncle.*—Shape: Square in cross section. Strength: Strong. Aspect: Erect. Length: Approximately 5 cm. Diameter: Approximately 2.0 mm. Texture: Pubescent with short, appressed hairs. Color: 144A along the center of each side and 148B overlain with 86B along all four edges.

Flower description:

*Bud rate of opening.*—Generally takes approximately 2 days for bud to progress from first color to fully open flower.

*Bud just before opening.*—Shape: Ovoid. Length: Approximately 8.3 mm. Diameter: Approximately 4.0 mm. Color: 89B.

*Type.*—Single, labiate. Flowers are persistent with a faint, sweet fragrance.

*Flower size.*—Length: Approximately 1.5 cm. Width: Approximately 6.6 mm. Depth: Approximately 6.4 mm.

*Aspect.*—Facing outward.

*Petals.*—Quantity: One upper lip and one lower lip with four lobes. Lips are fused at base.

*Upper lip.*—Shape: Ovate with revolute edges. Apex: Obtuse. Margin: Entire. Length from throat: Approximately 6.0 mm. Width: Approximately 1.9 mm. Texture of upper surface: Densely pubescent. Texture of lower surfaces: Glabrous. Color of upper surface: Between N88A and N89B. Color of lower surface: 86A.

*Lower lip.*—Shape: Obovate. Apex: Obtuse. Margin: Entire. Length of each central lobe from throat: Approximately 3.0 mm. Width of each central lobe: Approximately 1.9 mm. Length of each lateral lobe: Approximately 5.0 mm. Width of each lateral lobe: Approximately 3.0 mm. Texture of upper surface of all lobes: Glabrous. Texture of lower surface of all lobes: Densely pubescent. Color of upper surface of all lobes: N88B. Color of lower surface of all lobes: N88C with margin of N88B.

*Pedicel.*—Strength: Strong, flexible. Aspect: Acute angle to stem. Length: Approximately 2.0 mm.

Diameter: Approximately 0.4 mm. Texture: Pubescent. Color: 150A.

*Calyx.*—Shape: Tubular. Height: Approximately 7.0 mm. Width: Approximately 3.0 mm.

*Sepals.*—Quantity per flower: 2, fused to form a tube. Shape: Triangular. Apex: Apiculate. Margin: Entire. Sepal length: Approximately 7.0 mm. Sepal width: Approximately 4.0 mm. Texture of upper or inner surface: Glabrous. Texture of lower or outer surface: Lanate. Color of upper surface: 139D with N88B at margin of apex. Color of lower surface: 138D at base, 93A at apex.

*Reproductive organs.*—Androecium: Stamen quantity: 2. Stamen length: 7.0 mm. Filament color: Transparent with a touch of 94D along edges. Anther shape: Very narrowly elliptic. Anther length: Approximately 1.4 mm. Anther color: N92B. Pollen amount: None observed. Gynoecium: Pistil quantity: One per flower. Pistil length: Approximately 8.6 mm. Stigma shape: Two-parted, cleft. Stigma length: Approximately 1.5 mm. Stigma color: 93B. Style length: Approximately 5.5 mm. Style color: Colorless, opaque. Ovary length: Approximately 1.6 mm. Ovary texture: Glabrous. Ovary color: 154D, transparent.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Balsalmisp', substantially as herein shown and described.

* * * * *